(12) United States Patent
Martinez et al.

(10) Patent No.: US 10,872,683 B1
(45) Date of Patent: Dec. 22, 2020

(54) SYSTEM AND METHOD FOR CLINICAL STRUCTURED REPORTING

(75) Inventors: David A. Martinez, Mill Valley, CA (US); David K. Martinez, San Francisco, CA (US)

(73) Assignee: CLICKVIEW CORPORATION, San Francisco, CA (US)

( * ) Notice: Subject to any disclaimer, the term of this patent is extended or adjusted under 35 U.S.C. 154(b) by 400 days.

(21) Appl. No.: 12/276,174

(22) Filed: Nov. 21, 2008

Related U.S. Application Data

(60) Provisional application No. 60/989,797, filed on Nov. 21, 2007.

(51) Int. Cl.
*G16H 10/00* (2018.01)
*G16H 80/00* (2018.01)

(52) U.S. Cl.
CPC ............. *G16H 10/00* (2018.01); *G16H 80/00* (2018.01)

(58) Field of Classification Search
CPC ............... G06F 19/322; G06F 19/3487; G06F 19/3418; G06F 19/345; G06F 19/325
USPC ........................................................ 705/2–4
See application file for complete search history.

(56) References Cited

U.S. PATENT DOCUMENTS

| | | | |
|---|---|---|---|
| 5,778,345 A * | 7/1998 | McCartney | 705/2 |
| 8,200,505 B2 | 6/2012 | Walker | |
| 2002/0016719 A1 * | 2/2002 | Nemeth et al. | 705/2 |
| 2003/0014284 A1 * | 1/2003 | Jones | G06Q 30/02 705/3 |
| 2003/0083903 A1 * | 5/2003 | Myers | 705/2 |
| 2005/0148849 A1 * | 7/2005 | Heere | G06F 19/321 600/407 |
| 2006/0041836 A1 * | 2/2006 | Gordon et al. | 715/513 |
| 2006/0200034 A1 * | 9/2006 | Ricci et al. | 600/513 |
| 2006/0259855 A1 * | 11/2006 | Crucs | 715/517 |
| 2007/0088525 A1 * | 4/2007 | Fotiades | G06Q 50/24 702/131 |
| 2010/0225316 A1 * | 9/2010 | Jacob | G01N 24/08 324/309 |

* cited by examiner

*Primary Examiner* — Reginald R Reyes
(74) *Attorney, Agent, or Firm* — Troutman Pepper Hamilton Sanders LLP (Rochester)

(57) ABSTRACT

Systems and methods for generating clinical structured reports, allowing users to indicate findings from a medical examination without having to enter normal findings. In one aspect, a user selects a clinical structured report template for a particular type of medical examination. A default clinical structured report based on the template, and comprising normal findings for the medical examination type, is presented to the user. The user modifies one or more of the normal findings to indicate abnormal findings. A clinical structured report is generated, based on the default normal findings and the abnormal findings received from the user. The report is stored in a database or sent to one or more recipients over a network.

In one aspect, the normal findings comprise text data. In another aspect, the normal findings comprise plots, graphs, diagrams, or other types of data.

In one aspect, the system provides for multi-language support and translations. In one aspect, the clinical structured report is used to generate billing information. In one aspect, the clinical structured report is generated by a computer aided diagnosis tool.

18 Claims, 16 Drawing Sheets

201a

| Findings | | Edit |
|---|---|---|
| | ⨯ Check for Abnormal   Uncheck for Normal | |
| Liver and Spleen | ☐ The Liver appears normal in size and consistency. The hepatic parenchyma appears homogenous and normal in density. The Spleen appears normal in size and consistency.<br>Edit Comment | |

201b

| Findings | | Edit |
|---|---|---|
| | ⨯ Check for Abnormal   Uncheck for Normal | |
| Liver and Spleen | ☐ The Liver appears normal in size and consistency. The hepatic panenchyma appears homogenous and normal in density. The spleen appears normal in size and consistency. | |
| | Save Comment    Cancel \| Reset | |

201c

| Findings | | Edit |
|---|---|---|
| | ⨯ Check for Abnormal   Uncheck for Normal | |
| Liver and Spleen | ☐ The Liver appears normal in size and consistency.The hepatic panenchyma appears homogenous and normal in density. The spleen appears normal in size and consistency. MORE COMMENTS ADDED<br>Edit Comments | |

201d

| Findings | | Edit |
|---|---|---|
| | ⨯ Check for Abnormal   Uncheck for Normal | |
| Liver and Spleen | ☑ ☐ There are multiple focal areas measuring [   ] cm to [   ] cm in dimension of [         ] [▼] density in the [         ] [▼] see.<br>☑ There is a single local area measuring cm of [Increased ▼] attenuation in the [left lobe ▼] of the [liver ▼].<br>☑ The liver appears diffusely enlarged without focal defects and demonstrates a lower attenuation than the spleen, suggestive of fatty infiltration<br>☐ The liver appeas small and demonstrated increased attenuation suggestive of cirrhosis of uncertain cause.<br>Save Comment \| Cancel | |

201e

| Findings | | Edit |
|---|---|---|
| | ⨯ Check for Abnormal   Uncheck for Normal | |
| Liver and Spleen | ☑ There is a single focal area measuring cm of increased attenuation in the left lobe of the liver. The liver appears diffusely enlarged without focal defects and demonstrates a lower attenuation than the spleen, suggestive of fatty infiltration. | |
| | Save Comment    Cancel \| Reset | |

201f

| Findings | | Edit |
|---|---|---|
| | ⨯ Check for Abnormal   Uncheck for Normal | |
| Liver and Spleen | ☑ There is a single focal area measuring cm of increased attenuation in the left lobe of the liver. The liver appears diffusely enlarged without focal defects and demonstrates a lower attenuation than the spleen, suggestive of fatty infiltration. ADDED COMMENTS HERE<br>Edit Comments | |

Figure 2

| Clickview 7i - Patient Record - Test, CT - Microsoft Internet Explorer | | □ ⊡ ⊠ |
|---|---|---|
| File Edit View Favorites Tools Help | | |

Back

Address

CLICK✱VIEW®

◁ back to main page

Signed In: Peter Dale (Administration)  Logout  |  Edit Profile                                Help  [?]

Main Page > Patient Search Results

Patient Record: *Test, CT*

| Allergies/Medications | [?] |
|---|---|
| Allergies: None Selected Medications: None Selected | |

Test, CT

Edit This Patient
ID:              testct
DOB:
Age:
SSN:
Home:
Work:
Address:
E-mail:
Ref Phys:

---

Administrative Options

Delete Exams or Episodes
View Audit Log

---

Patient Search

Enter New Patient

Patient ID:
[        ]

Patient name (Last, First)::
[        ]

Social Security #:
[   ]-[   ]-[     ]

[ Search ]

Episode: 11/7/2007 - 11/16/2007                              New Episode

| Ultrasound | [?] |
|---|---|
| No Ultrasound Examinations | |
| Create new exam: OB | Fetal Assesment | Text | Gyn | General | |

| CT | [?] |
|---|---|
| Abdomen:   11/16/2007   >   *(Not Validated)* | |
| Brain/Head: 11/7/2007    >   *(Not Validated)* | |

Create new exam  Brain/Head  |  Abdomen

| MRI | [?] |
|---|---|
| Knee:   11/7/2007   >   *(Not Validated)* | |

Create new exam:  Knee  |  Shoulder  |  Lumbar Spine

| Superbill | [?] |
|---|---|
| Display patient codes by date: From: [10/1/2007] □  To: [10/31/2007] □  [ Superbill ] | |

Display all codes for this patient

Figure 3

○ Clickview 7i - Brain/Head Exam Wizard: Page 1 of 6. - Microsoft Internet Explorer  □ □ ⊠

File  Edit  View  Favorites  Tools  Help

○ Back  ○  □ □ ◯ ◯

Address [                              ]

CLICK✻VIEW®

Signed In: Peter Dale (Administration)                                    Help [?]

Main Page > Test, CT > Brain/Head Exam (11/7/2007) > Exam Info

| Test, CT | |
|---|---|
| ID: | testct |
| DOB: | |
| Age: | |
| Ref Phys: | |

Exam Information

Brain/Head Exam Wizard
Page 1 of 6    PREV  NEXT  SAVE

| Brain/Head Exam Wizard | |
|---|---|
| ▸ 1. Exam Info | |
| 2. Baseline | |
| 3. Intracranial | |
| 4. Orbits | |
| 5. Sinuses/Mastoid | |
| 6. Calvarium | |

Exam Date:  [11/7/2007]
Procedure:  [Brain/Head Survey ▼]
Exam Site:  [            ▼]
Contrast    [              ▼]
Slice
Thickness:
[                    ▼]

Accession #1:  [            ]

Study UID:     [                    ]

Ref Phys:   [        ▼]
Technician: [        ▼]

Premedication: ⦿ Yes  ○ No

History:
Headaches:      ☐
Dizziness:      ☐
Syncope:        ☐
TIA:            ☐
Stroke:         ☐
Carotid Bruit:  ☐
Blurry Vision:  ☐
Altered Gait:   ☐
Epilepsy:       ☐
Facial Trauma:  ☐
Head Trauma:    ☐
S/P Craniotomy: ☐
R/O Carcinoma:  ☐
Carcinoma, R/O Mets: ☐

[Next Page ➡]  [Save/Exit Exam Wizard ◇]

© 2002-2007 ClickView Corporation.

Figure 4

○ ClickView 7i - CV Worksheet - Microsoft Internet Explorer

File Edit View Favorites Tools Help

○ Back

Address

CLICK✱VIEW®

⬜ back to main page
⬜ back to patient record

Exams
Carotid:
 11/19/2007
Abdomen CT:
 11/18/2007
Brain/Head CT:
 ▸ 11/18/2007

View: ▸ Compact | Expanded

Validation
☑ Preliminary Read
☑ Sign Exam as Final

Publish This Report
🖨 Printable Report
🖨 Setup & Print
○ Fax This Report
✉ E-Mail This Report
□ Export This Report Audit
◇ View Log Signed In: Peter Dale (Administration)  Logout | Edit Profile          Help ?

Main Page > Test, Pelvis > CV Worksheet (11/18/2007)

CV Worksheet for Test, Pelvis

Brain/Head CT Exam, 11/18/2007

Move Exam to Folder: [New Folder] ▼ [Send]

Edit this exam:

Exam Info | Baseline | Intracranial | Orbits | Sinuses/Mastoid | Calvarium

Exam Info                                                                Edit

| Name:        | Test, Pelvis       | Exam Date:      | 11/18/2007 |
| Patient ID:  | testpelvis         | Exam Site:      | RSNA |
| DOB:         |                    | Procedure:      | Brain/Head CT Survey |
| Age:         |                    | Contrast:       | None Followed by Non-ionic (Ultravist 300) |
| Ref. Phys:   |                    | Slice Thickness:| 8 mm contiguous supratentorial, 5mm posterior fossa |
| History:     | Dizziness, Syncope.| Comparison:     | 7/01/2006 |
| Premedicaion: Yes. |              | Accession:      | 123456 |
|              |                    | Study UID:      | 1.1000.100000.123456789 |

Findings                                                                 Edit ⟳ Check for Abnormal. Uncheck for Normal.

| Intracranial | ☐ | The Cerebral Hemispheres and Posterior Fossa appear symmetrical with normal patterns of homogenous attenuation of grey and white matter. No areas of hemorrhage or focal abnormal attenuation are seen. Grey-white matter differentiation is normal. The third and fourth Ventricles are patent and normal in dimension and midline alignment. Edit Comments |
| 501a | | |
| 501b | ☐ Cerebral Hemispheres: | The cerebral hemispheres appear normal in size and attenuation for the patient's agw with no shift of the midline. Edit Comments |
| 501c | ☐ Ventricles: | The ventricles appear normal in size and appearance and are symmetrical in the midline with no shift, mass or hemorrhage |

Figure 5a

| | |
|---|---|
| ○ ClickView 7i - CV Worksheet - Microsoft Internet Explorer | □ ▣ ⊠ |

File  Edit  View  Favorites  Tools  Help

○ Back  ○  ▢ ▢ ⌂ ⌃

Address [                                        ]

✉ E-Mail This Report
▢ Export This Report

Audit

◇ View Log

Findings                  Edit

⌅ Check for Abnormal. Uncheck for Normal.

| | | | |
|---|---|---|---|
| Intracranial | 501a | ▢ | The Cerebral Hemispheres and Posterior Fossa appear symmetrical with normal patterns of homogenous attenuation of grey and white matter. No areas of hemorrhage or focal abnormal attenuation are seen. Grey-white matter differentiation is normal. The third and fourth Ventricles are patent and normal in dimension and midline alignment. <u>Edit Comments</u> |
| | 501b | ▢ Cerebral Hemispheres: | The cerebral hemispheres appear normal in size and attenuation for the patient's agw with no shift of the midline. <u>Edit Comments</u> |
| | 501c | ▢ Ventricles: | The ventricles appear normal in size and appearance and are symmetrical in the midline with no shift, mass or hemorrhage apparent. The Third and Fourth Ventricles are patent and normal in dimension. <u>Edit Comments</u> |
| | 501d | ▢ Posterior Fossa: | The cerebellum, midbrain, pons and medulla are visualized and appear normal in size, symmetry and attenuation. The fourth ventricle is patent and normal in dimension. <u>Edit Comments</u> |
| | 501e | ▢ Sulci: | The major and minor sulci are well visualized and appear normal for the patient's age. <u>Edit Comments</u> |
| | 501f | ▢ Extra-axial Space: | The Extra-Axial space appear's normal with no areas of abnormal attenuation <u>Edit Comments</u> |
| Orbits | 501g | ▢ | Axial and Coronal sections were obtained through the orbits. The muscle cone, globes, optic nerves, ophthalmic arteries and optic nerve sheathes bilateraly were observed and appear normal. The bony orbital structures appear intact. <u>Edit Comments</u> |
| Sinuses/Mastoid | 501h | ▢ | Axial and Coronal sections were obtained through the paranasal sinuses. The paranasal sinuses appear normally aerated with normal appearing symmetry. No space occupying lesions were noted. No opacification of the sinuses was noted. Bony structures appear normal. The mastoids were normally aerated with no apparent opacification or mass lesions. <u>Edit Comments</u> |
| | 501i | ▢ Frontal: | The frontal sinuses are normal in appearance. <u>Edit Comments</u> |
| | 501j | ▢ Maxillary: | The Maxillary sinuses are normal in appearance. <u>Edit Comments</u> |
| | 501k | ▢ Mastoid: | The mastoid bones and auditory canals appear normal bilaterally. <u>Edit Comments</u> |
| Calvarium | | ▢ | The Frontal, Parietal, Temporal and Occipital bones appear normal with no areas |

Figure 5b

| | | |
|---|---|---|
| | | Edit Comments |
| | 501i | ☐ Frontal: The frontal sinuses are normal in appearance. Edit Comments |
| | 501j | ☐ Maxillary: The Maxillary sinuses are normal in appearance. Edit Comments |
| | 501k | ☐ Mastoid: The mastoid bones and auditory canals appear normal bilaterally. Edit Comments |
| | Calvarium 501L | ☐ The Frontal, Parietal, Temporal and Occipital bones appear normal with no areas or abnormal attenuation or fracture. Edit Comments |
| | 501m | ☐ Frontal Bone: The Frontal bones appear normal bilaterally. Edit Comments |
| | 501n | ☐ Parietal: The Parietal bones appear normal bilaterally. Edit Comments |
| | 501o | ☐ Temporal: The temporal bones appear normal bilaterally. Edit Comments |
| | 501p | ☐ Occipital Bone: The occipital bone appears normal. Edit Comments |

Impressions and Recommendations

502      Click here to start Impressions and Recommendations

This exam has not been signed and is not a final report.
Click Here to Validate

Allergies

Medications

Exam Status

*Last Changed By: Peter Dale,   11/18/2007   7:08:04 PM   View Audit Log.*

© 202-2007 ClickView Corporation.

Figure 5c

| | | Edit Comments | |
|---|---|---|---|
| | 501i | ☐ Frontal: | The frontal sinuses are normal in appearance. Edit Comments |
| | 501j | ☐ Maxillary: | The Maxillary sinuses are normal in appearance. Edit Comments |
| | 501k | ☐ Mastoid: | The mastoid bones and auditory canals appear normal bilaterally. Edit Comments |
| | Calvarium 501L | ☐ | The Frontal, Parietal, Temporal and Occipital bones appear normal with no areas or abnormal attenuation or fracture. Edit Comments |
| | 501m | ☐ Frontal Bone: | The Frontal bones appear normal bilaterally. Edit Comments |
| | 501n | ☐ Parietal: | The Parietal bones appear normal bilaterally. Edit Comments |
| | 501o | ☐ Temporal: | The temporal bones appear normal bilaterally. Edit Comments |
| | 501p | ☐ Occipital Bone: | The occipital bone appears normal. Edit Comments |

Impressions and Recommendations

502 — Normal Brain/Head CT exam.

Save Impressions and Recommendations    Reset

This exam has not been signed and is not a final report.
Click Here to Validate

Allergies

Medications

Exam Status

*Last Changed By: Peter Dale,   11/18/2007   7:08:04 PM   View Audit Log.*

Figure 5d

| | | Edit Comments | |
|---|---|---|---|
| | 501i | ☐ Frontal: | The frontal sinuses are normal in appearance.<br>Edit Comments |
| | 501j | ☐ Maxillary: | The Maxillary sinuses are normal in appearance.<br>Edit Comments |
| | 501k | ☐ Mastoid: | The mastoid bones and auditory canals appear normal bilaterally.<br>Edit Comments |
| | Calvarium<br>501L | ☐ | The Frontal, Parietal, Temporal and Occipital bones appear normal with no areas or abnormal attenuation or fracture.<br>Edit Comments |
| | 501m | ☐ Frontal Bone: | The Frontal bones appear normal bilaterally.<br>Edit Comments |
| | 501n | ☐ Parietal: | The Parietal bones appear normal bilaterally.<br>Edit Comments |
| | 501o | ☐ Temporal: | The temporal bones appear normal bilaterally.<br>Edit Comments |
| | 501p | ☐ Occipital Bone: | The occipital bone appears normal.<br>Edit Comments |

Impressions and Recommendations

502  Normal Brain/Head CT exam.

Click here to edit Impressions and Recommendations

This exam has not been signed and is not a final report.
Click Here to Validate

Allergies

Medications

Exam Status

*Last Changed By: Peter Dale,   11/18/2007   7:08:04 PM   View Audit Log.*

Figure 5e

○ ClickView 7i - CV Worksheet - Microsoft Internet Explorer

File Edit View Favorites Tools Help

○ Back

Address

Knee MRI:
11/18/2007

View: ▸ Compact | Expanded

Exam Options
☐ Comments Worksheet
☐ Consultation Letter

Validation
☐ Preliminary Read
☐ Sign Exam as Final

Publish This Report
🗄 Printable Report
🖨 Setup & Print
○ Fax This Report
✉ E-Mail This Report
🗔 Export This Report

New Exams
New OB Exam
New Fetal Assessment Exam
New Text Exam
New Gyn Exam
New General Exam Delete Exams

Patient Search
Enter New Patient

Exam Info | Baseline | Intracranial | Orbits | Sinuses/Mastoid | Calvarium

Exam Info                                                                                           Edit Name:          Test, CT                    Exam Date:      11/7/2007
Patient ID:    testct                      Exam Site:      RSNA
DOB:                                       Procedure:      Brain/Head CT Survey
Age:                                       Contrast:       None Followed by Non-
                                                           ionic (Ultravist 300)
Ref. Phys:                                 Slice Thickness: 8 mm contiguous
                                                           supratentorial, 5mm
History:       Dizziness, Syncope.                         posterior fossa
                                           Comparison:     7/01/2006
Premedicaion: Yes.
                                           Accession:      123456
                                           Study UID:      1.1000.100000.123456789

Findings                                                                                            Edit ⤓ Check for Abnormal. Uncheck for Normal.

| Intracranial | ☐ Edit Comments | |
| --- | --- | --- |
| 501a | ☐ Cerebral Hemispheres: | The Cerebral Hemisphere, Ventricles, Posterior Fossa appear symmetrical, homogenous in attenuation of grey and white matter with no apparent lesions. No areas of hemorrhage or focal abnormal attenuation are seen. Grey-White Matter Differentiation is normal. The Third and Fourth Ventricles are patent and normal in dimension. |
| | | Save Comment         Cancel | Reset |
| 501b | ☑ Ventricles: | There is a single area of abnormal focal density in the anterior horn of the left ventricle. Calcification is seen. Peripheral edema is seen. There is shift of the midline. Edit Comments |
| | ☐ Posterior Fossa: | The cerebellum, midbrain, pons and medulla are visualized and appear normal in size, symmetry and attenuation. The fourth ventricle is patent and normal in dimension. Edit Comments |
| | ☐ Sulci: | The major and minor sulci are well visualized and appear normal for the patient's age. Edit Comments |
| | ☐ Extra-axial space: | The Extra-Axial space appears normal with no areas of abnormal attenuation. |

| Brain/Head CT Exam for Test, CT: 11/7/2007. - Microsoft Internet Explorer |
|---|

File  Edit  View  Favorites  Tools  Help

◯ Back

Address

Clickview Corporation
944 Market St.
Suite 402
San Francisco, CA 94102
800.628.0020
fax 415.693.9494

CLICK✱VIEW®
C  O  R  P  O  R  A  T  I  O  N

Test, CT                               Brain/Head CT Exam, 11/7/2007

| Exam Information |
|---|
| This is a DRAFT REPORT. |

Name:       Test, CT              Exam Date: 11/7/2007           OB Hx:  G:       ( )
Patient ID: testct                 Procedure:                            F Trim:  ( )
DOB:                               Exam Site:                            Pre:     ( )
Age:                                                                     Ab-I:    ( )
                                                                         Ab-S:    ( )
                                                                         Ect:     ( )
                                                                         Multi:   ( )
                                                                         Liv:     ( )

| Findings | | | |
|---|---|---|---|
| | Intracranial | Cerebral Hemispheres: | The Cerebral Hemispheres, Ventricles, Posterior Fossa appear symmetrical, homogenous in attenuation of grey and white matter with no apparent lesions. No areas of hemorrhage or focal abnormal attenuation are seen. Grey-White Matter Differentiation is normal. The Third and Fourth Ventricles are patent and normal in dimension. |
| | | Ventricles: | There is a single area of abnormal focal density in the anterior horn of the left ventricle. Calcification is seen. Peripheral edema is seen. There is shift of the midline. |
| | | Posterior Fossa: | The cerebellum, midbrain, pons and medulla are visualized and appear normal in size, symmetry and attenuation. The fourth ventricle is patent and normal in dimension. |
| | | Sulci: | The major and minor sulci are well visualized and appear normal for the patient's age. |
| | | Extra-axial space: | The Extra-Axial space appears normal with no areas of abnormal attenuation. |
| | Orbits | | Axial and Coronal sections were obtained through the orbits. The muscle cone, globes, optic nerves, ophthalmic arteries and optic nerve sheathes bilaterally were observed and and appear normal. The bony orbital structures appear intact. |
| | Sinuses/Mastoid | | Axial and Coronal sections were obtained through the paranasal sinuses. The paranasal sinuses appear normally aerated with normal appearing symmetry. No space occupying |

SYSTEM AND METHOD FOR CLINICAL STRUCTURED REPORTING

CROSS-REFERENCES TO RELATED APPLICATIONS

This application claims priority to U.S. Provisional Patent Application No. 60/989,797 filed on Nov. 21, 2007.

BACKGROUND

Field

The present invention generally relates to document generation, and in particular to creating a clinical structured report.

Background of the Invention

In many industries, such as the healthcare industry, technicians or specialists evaluate data and generate written reports to be utilized by others in providing a service or product. Other individuals refer to the written reports to provide the appropriate service or product to the consumer. The process of creating the written reports, however, is a time-consuming and expensive process.

For example, radiologists diagnose diseases by analyzing radiological images and generate written reports describing their findings. One technology available to such specialists is the use of dictation systems, such as a Dictaphone. The tapes are picked up by transcriptionists and taken off-site for transcription. Approximately 24-48 hours later, the transcribed reports are returned to the radiologist for corrections. The marked reports are picked up by the transcriptionists and taken off-site for correction. The radiologists and the transcriptionists continue in this manner until all corrections have been incorporated into the transcribed report. Finally, the radiologist signs the corrected reports, and the corrected reports are made available for distribution via runners, who typically hand-carry the corrected reports to the requesting physicians.

Technologies such as fax and e-mail have eliminated the step of physically picking up the reports, thus, decreasing the amount of time required to produce the corrected reports. These technologies, however, fail to significantly impact the timeliness of the production of such reports.

Tele-transcription systems reduce the dictation and transcription time because the systems allow radiologists to pick up an ordinary phone and dial into a dictation system provider and report their cases. These systems eliminate the runners and cut transcription turnaround time significantly, to about 12-24 hours. Corrections to the reports, however, are still time-consuming.

Some systems utilize voice recognition technology in an attempt to reduce the dictation/transcription time. These voice recognition systems, however, have to be trained to each speaker's specific voice recognition patterns, and the accuracy rates are too low for many applications, including radiology in which an accuracy rate of 95% is not acceptable. Corrections in many of these systems are even more cumbersome, and the systems are expensive. Although the voice recognition system provides many advantages, such as the electronic distribution of reports, the disadvantages discussed above limit its usefulness.

Another technology available to such specialists is the use of electronic data entry systems, such as those utilizing hierarchical input nodes, similar to those mechanisms employed by programs such as Microsoft Corporation's Windows Explorer program. Such systems require a user to select a parent node, the selection of which displays several child nodes. The user selects a child node, which may, in turn open up several other nodes. The parent node may describe general parts of the anatomy. The child node may describe sub-parts of the anatomy. The user thus searches through the node tree to find the appropriate node and selects that node. The selection of this node prompts the system to add a text to the report. Such techniques have several shortcomings in the medical context. For example, such hierarchical trees can be very large and complex. A user is forced to search through the entire tree to find the desired node, or to select through several hierarchies to find the desired node. Further, the user goes through the process of selecting a node for each line of the report that the user wants to generate. Such a system is both time-consuming and can be confusing, as a user not familiar with the layout of the nodal hierarchy will have to search the entire hierarchy for the desired selection.

Other systems employ a combination of node selection and voice recognition to generate radiology reports. Users of such systems select a single node to generate a normal report, and use voice recognition technology to dictate a report with a finding of a medical abnormality. Such a system is prone to the same errors previously described with respect to voice recognition technology.

The systems described generally begin with a blank report. The user populates the report by adding material to the blank report. Medical reports are required to contain significant amounts of detail for medical billing practices (particularly promulgated by the insurance industry). This is true even if the report denotes normal or healthy findings. Statistically, a significant proportion of medical reports, particularly radiology reports, are normal. Thus, systems that begin with a blank report for the user to populate with normal as well as abnormal findings are both costly and time-consuming for an industry where the significant proportion of such reports are normal and contain similar text and values.

The systems described are also plain text reports, and the consumer of that report must read carefully through the report in order to discern whether the report discloses any medical abnormalities. Such a system is prone to errors in fast-paced environments, where a medical abnormality thus reported may be overlooked.

Furthermore, the systems described generally do not provide the reports in an electronic form that enables a user to search across reports and create reports based on the content of a plurality of previously completed reports. Rather, the systems generally only provide the ability to search for specific strings of text contained within a report.

Therefore, the present invention advances the art by providing an improved technique that allows users to generate clinical reports.

SUMMARY OF THE INVENTION

Systems and methods for generating clinical structured reports, allowing users to indicate findings from a medical examination without having to enter normal findings. In one aspect, a user selects a clinical structured report template for a particular type of medical examination. A default clinical structured report based on the template, and comprising normal findings for the medical examination type, is presented to the user. The user modifies one or more of the normal findings to indicate abnormal findings. A clinical structured report is generated, based on the default normal findings and the abnormal findings received from the user. The report is stored in a database or sent to one or more recipients over a network. In one aspect, the normal findings comprise text data. In another aspect, the normal findings comprise plots, graphs, diagrams, or other types of data.

In one embodiment, the system provides for multi-language support and translations. In one embodiment, the clinical structured report is used to generate billing information. In one embodiment, the clinical structured report is generated by a computer aided diagnosis tool.

BRIEF DESCRIPTION OF DRAWINGS

Referring now to the drawings in which like reference numbers represent corresponding parts throughout:

FIG. 2 illustrate example portions of an initial clinical structured report, in accordance with an embodiment of the present invention.

FIGS. 3 and 4 illustrate example user interfaces for creating a clinical structured report, in accordance with an embodiment of the present invention.

FIGS. 5A-5F illustrate different views of one particular example of a structured clinical report.

FIG. 6 illustrates a clinical structured report created in accordance with an embodiment of the present invention. Specifically, the figure illustrates further user interface elements for selecting or specifying an abnormality.

FIG. 7 illustrates a completed clinical structured report in accordance with an embodiment of the present invention.

FIG. 8 illustrates the choice of various templates for a set of example clinical structured reports according to embodiments of the present invention.

FIG. 9 illustrates the consequence of selecting a template of a clinical structured report of FIG. 8, in accordance with an embodiment of the present invention.

FIG. 10 illustrates the consequence of selecting a template of a clinical structured report of FIG. 9, as well as the ability to edit the standard normal templates of the clinical structured report in accordance with embodiments of the present invention.

DETAILED DESCRIPTION

Figure 1:
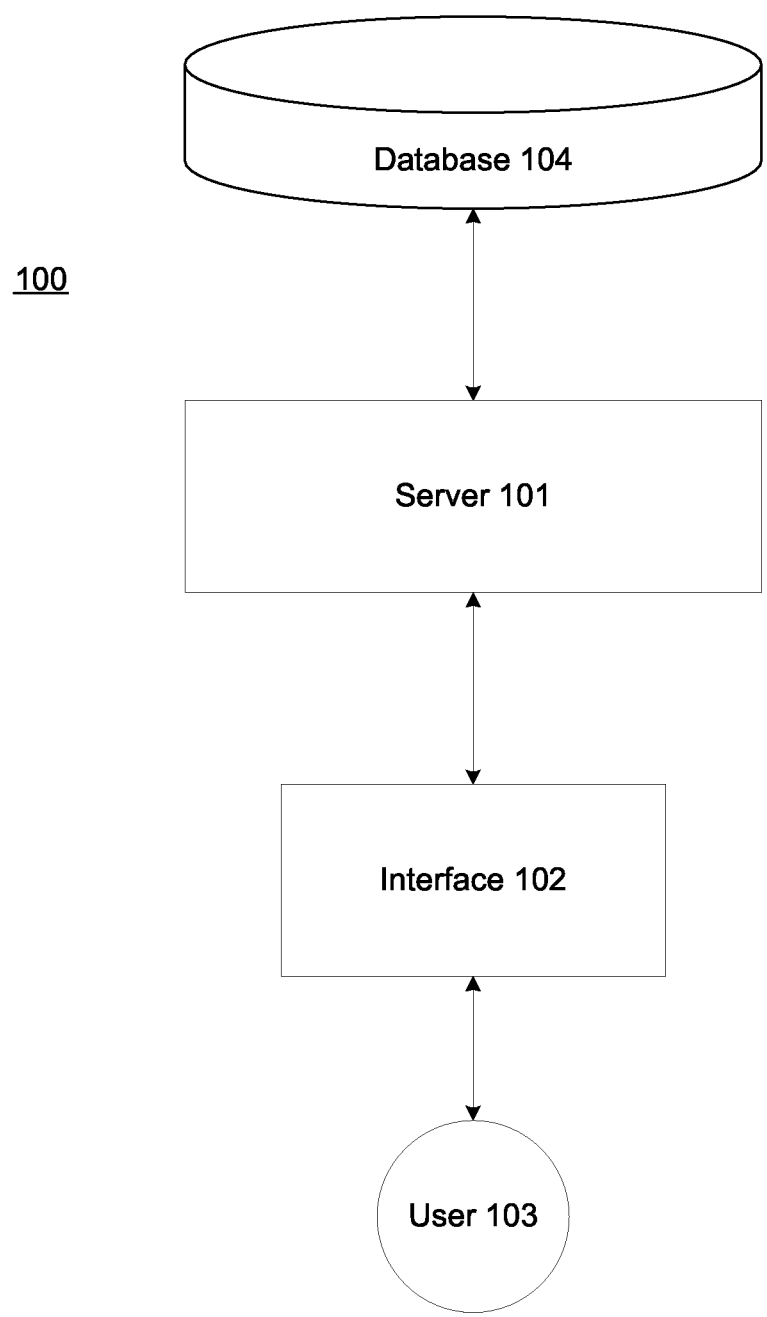
FIG. 1 illustrates a system for creating and managing clinical structured reports, in accordance with an embodiment of the present invention.

In the following description, for purposes of explanation, numerous specific details are set forth in order to provide a thorough understanding of the invention. It will be apparent, however, to one skilled in the art that the invention can be practiced without these specific details.

It is further noted that, unless otherwise indicated, all functions described herein may be performed by either hardware or software, or some combination thereof. In a preferred embodiment, however, the functions are performed by a processor such as a computer or an electronic data processor in accordance with code such as computer program code, software, and/or integrated circuits that are coded to perform such functions, unless otherwise indicated.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

As employed herein, the term "patient" shall mean a living member of the animal kingdom including human beings.

The present invention provides a method for generating a clinical structured report. As one of ordinary skill in the art will appreciate, the present invention applies to any area in which a report is to be generated for use by other individuals or groups. For example, an embodiment of the present invention may be utilized in radiological, toxicological, pharmaceutical, other healthcare specialties, or the like. For illustrative purposes only, however, the following description generally provides examples specific to one or more types of reports, such as radiology and reports generated by radiologists, radiology technicians, or other radiology support staff.

As will be discussed in greater detail below, an embodiment of the invention allows a user to generate clinical structured reports from a default template pre-filled to show normal radiology findings. For example, the radiologist or user can use and access an embodiment of the invention on a computer to generate a radiology report. An embodiment of the invention displays a default template showing descriptions or values indicative of normal radiology findings to the user. The normal values describe names and normal characteristics of both the general and specific anatomy that is the subject of the radiology report.

A user interface displays the default report and includes one or more user interface elements for confirming the values shown in the default report. Such a confirmation generates a report showing that general and specific anatomy exhibit normal characteristics. The user interface also displays one or more user interface elements for allowing users to indicate that some of the findings in the radiology exam at hand indicate one or more abnormalities (hereinafter also referred to as abnormal findings). Such a selection will preferably prompt the user to input the specifics of the abnormality, for example via one or more drop down menus or optionally through manual entry of the details of the abnormality. In one embodiment, the normal findings comprise text data. In other embodiments, the normal findings may also comprise plots, graphs, diagrams, or other types of data.

Referring to FIG. 1 of the drawings, the reference numeral 100 generally designates a reporting system, which embodies features of the present invention. Generally, the reporting system 100 comprises one or more interface devices 102, such as computers, cell phones, appliances, personal digital assistants (PDAs), television systems, etc. The interface device 102 preferably includes a processor, one or more data communications devices (e.g., modems, network interfaces, etc.), a monitor (e.g., CRT, LCD display, etc.), and one or more input devices (e.g., a mouse and/or a keyboard). It is envisioned that attached to the client computer may be other devices such as random-access memory (RAM), read-only memory (ROM), a video card, bus interfaces, printers, and the like. The interface device 102 is configured to allow a user 103 to enter data regarding observations that user 103 has made regarding a subject, patient, or image (not shown). For the purposes of describing the invention, user 103 will have the same meaning as "user" or "users".

Optionally, the interface device 102 is coupled to a server 101. The server 101 is preferably coupled to a database 104, which receives, stores, and sends data generated by one or more users. Database 104 also receives, stores, and sends default or modified templates that are used to generate clinical structured reports, in accordance with an embodiment of the present invention. Changes to the templates stored in database 104 are reflected in the generated reports. The server 101 is preferably a server accessible via an internal network to enable sharing of templates, generated data, and reports. Optionally, server 101 is also accessible via an external network, such as the Internet, to which the interface device 102 couples via a communications link, such as a TCP/IP communications link, a wireless communications link, or the like. The present embodiments allow for single user as well as multi user configurations. One or more users may be interacting with the system concurrently or sequentially when performing tasks such as viewing a report, filling a report, modifying a report or template or interacting with a system in any other way as described herein.

Figure 1A:
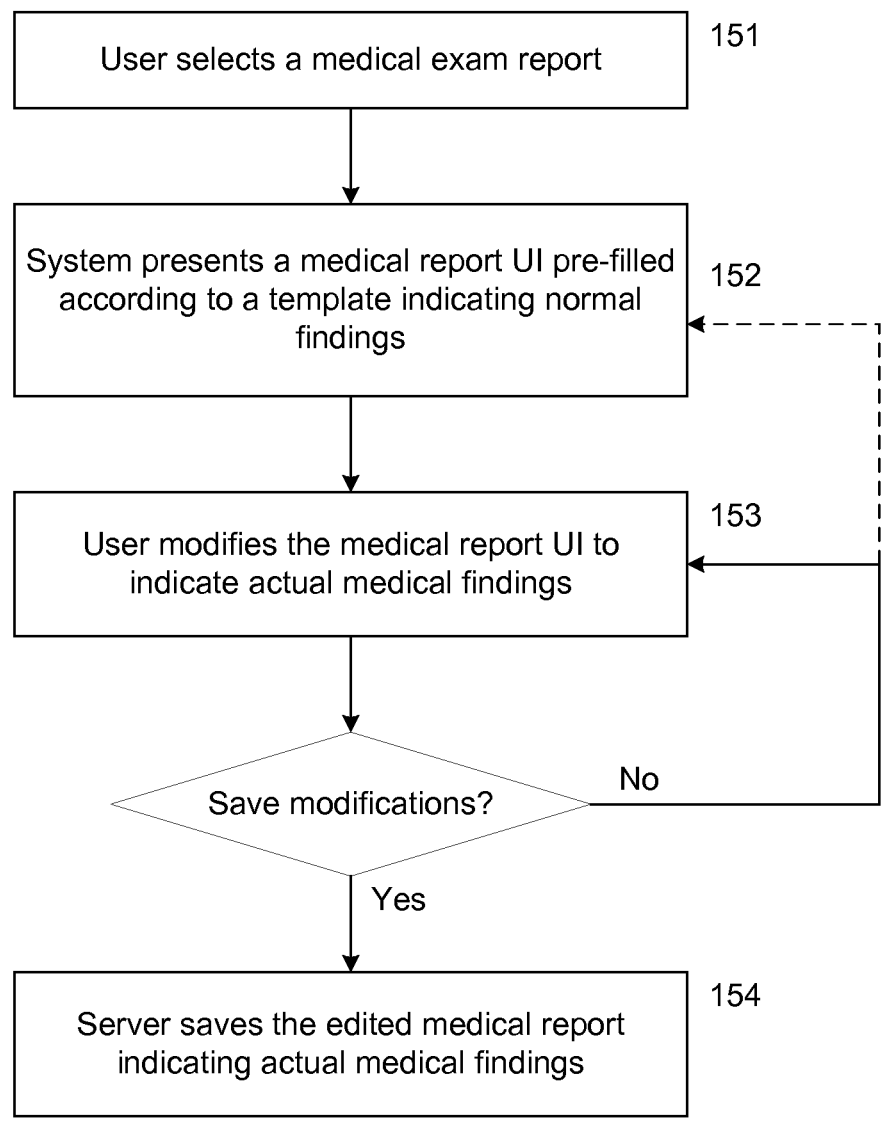
FIG. 1A is a flow diagram illustrating the process of generating a clinical structured report, in accordance with one embodiment of the present invention.

FIG. 1A is a flow diagram illustrating the process of generating a clinical structured report, in accordance with one embodiment of the present invention. At step 151, a user selects a report for a medical examination. At step 152, a user interface is presented to the user, the user interface indicating the selected report and initialized from a template comprising pre-filled values denoting normal findings for the selected medical exam. An example portion of such an initial report user interface is shown in FIG. 2, illustrating a portion of an example report for a medical exam of the liver and spleen as the report evolves according to the various steps of FIG. 1A. While the example report shown in FIG. 2 is generated from an exemplary template with pre-filled values denoting a normal medical exam of the liver and spleen, it is understood that this represents an exemplary embodiment and that reports for other medical exams can be generated in a similar manner.

At step 153, the user may modify the presented report user interface, which indicates pre-filled normal findings, in order to indicate actual findings from an actual medical exam. The user may do this, for example, by electing to edit the comments, as shown in the user interface 201a of FIG. 2. User interface 201b shows what is displayed to the user upon clicking an exemplary "Edit Comment" button of user interface 201a. Upon completion of the edit, the user may save the edited comment, for example by clicking a "Save Comment" button on the user interface of user interface 201b, upon which server 101 stores the edited comments into database 104, reflecting the actual medical findings as indicated and saved by the user. Upon storage of the actual findings, a user interface 201c is displayed to the user, presenting the user's modifications. For illustrative purposes, this is shown in user interface 201c of FIG. 2 using the phrase "MORE COMMENTS ADDED."

Alternatively, the user may choose to cancel the most recent edits, for example by clicking on a "Cancel" button as shown in interface 201b, upon which time the original user interface 201a is displayed to the user again. Alternatively, the user may choose to reset the presented user interface according to the pre-filled normal findings of the particular medical report template, for example by clicking on the "Reset" button as shown as shown in interface 201b, upon which time the Server 101 retrieves the normal findings from database 104 (or from a cache) and presents them once again as in user interface 201a.

Still referring to FIG. 2, the user may also interact with user interface 201a in a more structured fashion in order to denote an abnormality, for example by clicking the "Check for Abnormal" checkbox. The server 101 may then present to the user a more structured interface, for example such as interface 201d of FIG. 2, prompting the user to input further information regarding the abnormality. The server 101 and database 104 may be configured to present any suitable interface for entering abnormal findings, as appropriate for the particular medical report and as depending on any other relevant factors. The user may interact with user interface 201d to indicate one or more abnormal findings, and may then save the findings, for example by clicking on a "Save Comment" button as shown in 201d. Thereupon, the server 101 saves the findings, and subsequently presents a user interface indicating the user's findings in text form, such as shown in interface 201e. The user may continue to interact with user interface 201e to refine the next form of the findings, for example to add more comments. When done, the user may click on "Save Comments" to save the edits, whereupon the server 101 may present user interface 201f to the user indicating the user's edited findings. At this point, the user may indicate completion, or the user may alternatively further interact with interface 201f to "Edit Comments" (going back to 201e) or choose "Reset" (going back to 201d).

FIGS. 3 and 4 illustrate the process of accessing a template for a clinical structured report in accordance with an embodiment of the present invention. FIG. 3 illustrates a general patient file that user 103 may access via a database or through a network. User 103 selects "Create a New Exam" in order to initiate the creation of a new clinical structured report for the selected patient. FIG. 4 illustrates a consequence of selecting "Create a New Exam" in FIG. 3. FIG. 4 illustrates the retrieval or entry of the details of the patient's examination, the details being optionally retrieved from commonly utilized hospital network systems such as Hospital Information Systems (HIS), Radiology Information Systems (RIS), Picture Archiving Communications Systems (PACS), or other suitable system.

The clinical structured report comprises of one or more sections to indicate normal clinical or medical findings, and preferably one or more sections containing patient identifying information. FIGS. 5A-5C illustrate different views of one particular example of a structured clinical report (as indicated by the scroll bar on the right). The example report shown is a radiology report, and has sections 501a, 501b, 501c, 501d, 501e, 501f, 501g, and so on (best seen in FIG. 5B). As described above, these sections are pre-filled from a normal radiology template in order to indicate normal radiology findings. Preferably, these findings describe both the general and specific anatomy of the radiology subject, though the individual sections need not necessarily correspond directly to only one named part of the subject's anatomy. For example, report 501 is a CT Scan of the Brain/Head, the sections 501a through 501f (best seen in FIG. 5B) are found within the general anatomical description "Intracranial," referring to the general intracranial portions of the Brain/Head. However, in the particular example best seen in FIG. 5B, sections 501a through 501f (best seen in FIG. 5B) comprise descriptions of those specific portions of anatomy, and descriptions of the normal characteristics of those anatomies. For example, section 501*a* indicates "Cerebral Hemispheres" and includes a description of medically or clinically normal cerebral hemispheres.

Referring to FIG. 5C, to produce a radiology report indicating no abnormalities, user 103 interacts with an element of the user interface, for example by clicking on "Click Here to Validate". Thus, a detailed report is produced by minimal interaction with the user, in this particular example via one click. This system is desirable for hospitals, where a significant proportion of reports are normal, as it drastically reduces the production time for documents and reduces errors associated with voice recognition technology. Furthermore, it promotes linguistic and visual uniformity of medical reports.

Figure 6:
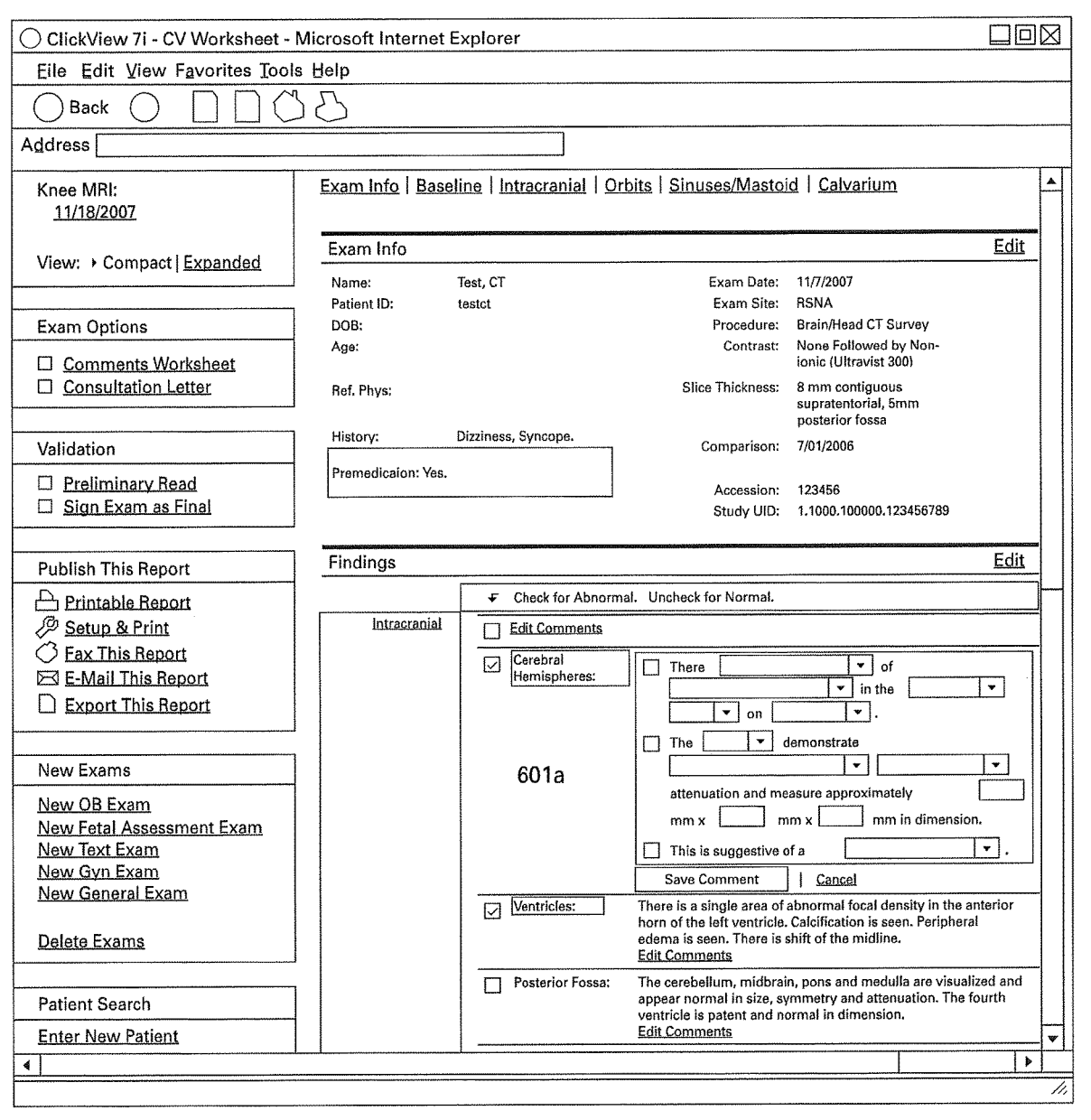

To produce a report indicating the presence of abnormalities, user 103 may disaffirm the report by interacting with an element of the user interface, for example by clicking a box under the heading "Check for Abnormal" (the heading is best seen in FIG. 5A). A selection of "Abnormal" prompts the user 103 to enter further information about the abnormality into the report. FIG. 6 shows an example user interface for accepting such information from user 103. In one embodiment, the prompt includes a series of one or more check boxes and/or drop-down menus with pre-filled portions of text. Once the user 103 indicates his selections, the selections are assembled into a data structure indicating a paragraph or other structure for storage in database 104.

Alternatively, the user interface may include a text box (as seen in FIGS. 5C, 5D, and 5E, section 502), which the user 103 can modify with any desired text.

Alternatively, for either a normal or abnormal report, user can modify the pre-existing template through entry into a text box (as shown in FIG. 5F, section 501*a*).

Referring to FIG. 7, optionally the clinical structured report thus produced comprises visual cues such as highlights or flags of any fields marked as abnormal. In one embodiment, such visual cues appear at the various stages of producing the report. For example, the parts of the report shown in FIG. 7 denoting an abnormality may be highlighted with visual cues. As another example, the parts of the working report shown in FIGS. 5D and 6 denoting the abnormality may be highlighted as well. Further, the report may be generated on a screen or other suitable electronic display, in a paper printout, in an electronic document, on a storage medium, or in any other suitable format. Inclusion of visual cues is advantageous, especially in a fast-paced environment where abnormalities may be overlooked or need to be called out visually for additional convenience or safety.

Figure 8:
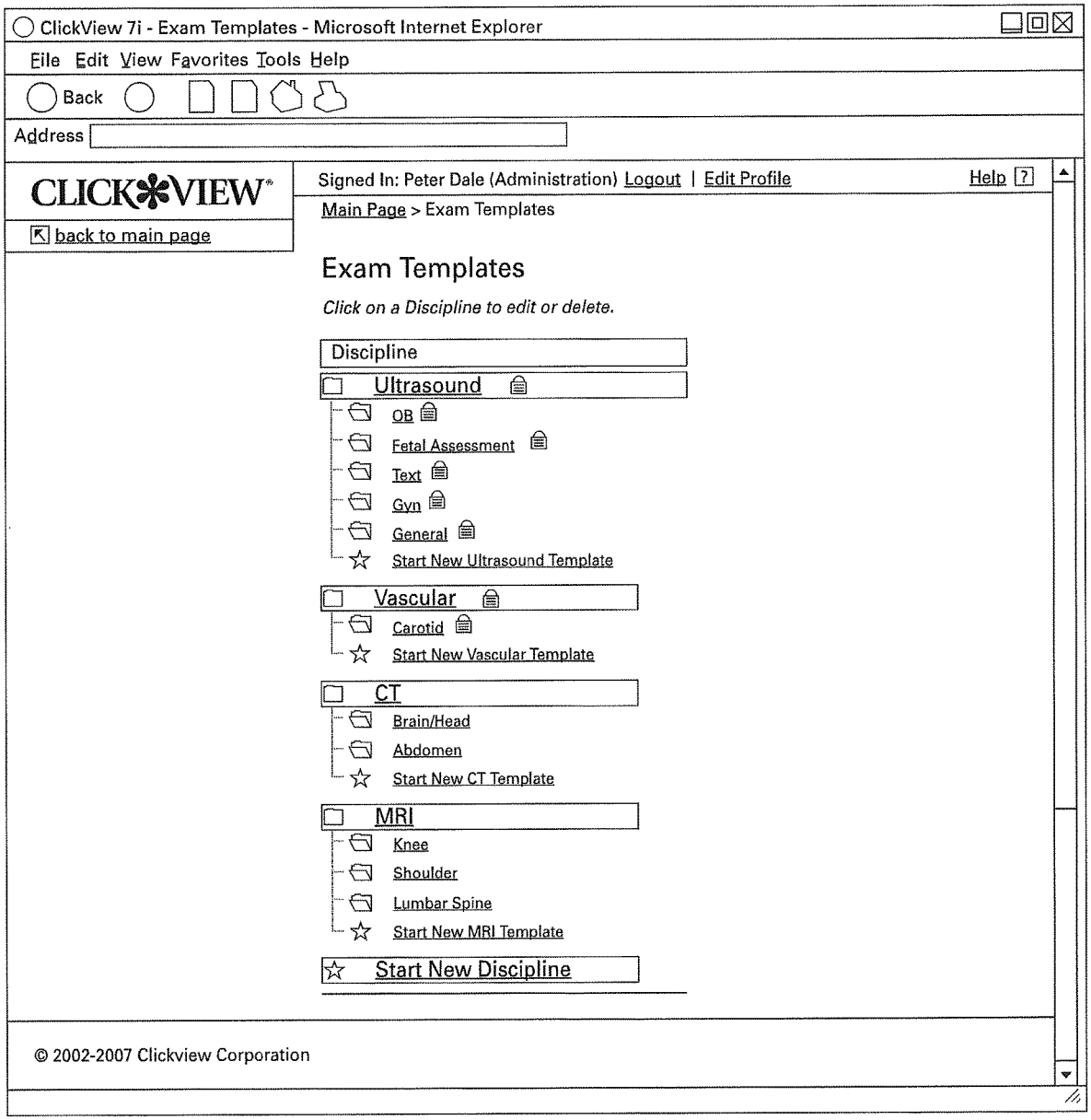
FIGS. 8-10 illustrate user interface elements for modifying a template for an example clinical structured report in accordance with an embodiment of the present invention.
Figure 9:
Figure 10:

A user may customize an existing template or create a new template. FIGS. 8, 9, and 10 illustrate the process of such customization. FIG. 8 illustrates the starting point for the customization of an existing template for an example abdominal exam. User 103 selects one of the template reports to modify, for example by clicking on it. Optionally, once user 103 selects the template, the user is presented to a user interface for selecting from one or more specific sub-templates, for example such as shown in FIG. 9. In the example shown, user 103 selects from one or more specific sub-templates in the menu on the left hand side of the screen.

Optionally, once user 103 selects a sub-template, the user is presented with an interface, such as the screen shown in FIG. 10, showing a modifiable template. The modifiable template comprises one or more sections, shown here as sections 1001*a* and 1001*b*, which will allow the user to pre-fill values for both normal and abnormal radiological reports, thereby defining the template.

While the above embodiments have been described generally with respect to normal and abnormal findings that are represented in text form, it is an advantageous aspect that the clinical structured reports may optionally comprise non text data, such as data plots, diagrams, images, etc., as will be presently described.

For example, in a medical ultrasound examination of an obstetrical patient, an ultrasound operator may measure one or more fetal biometrics. For example, the ultrasound operator may measure the size of certain elements of the fetal anatomy, such as the head, abdomen, extremities, etc. This ultrasound image data is then transferred from the ultrasound equipment into a database, such as database 104 or other database, as part of the patient's record (i.e. the mother, in this case). Such ultrasound image data often represents a significant portion of the patient's periodic ultrasound examination results. The system 100 may be configured to apply one or more mathematical computations (such as regressions, standard deviations, etc.) for fetal growth, as are known in the art, to the data stored in the database 104. For example, such computations may be applied to the fetal age, fetal weight, or to other data gathered from the examination. Results of such computations may then serve as statistical data points which can be correlated with the various dates of the periodic ultrasound examinations which are generally performed throughout the pregnancy. For example, such data points may be tracked graphically as serial data points plotted on a trend line to display progress of normal or abnormal fetal growth. A clinical structured report, as described herein, may comprise pre-filled graphical representations based on normal data points that are indicative of normal fetal growth, and which are part of an obstetrical ultrasound examination template stored on database 104. The actual data produced by the examination may then be used to juxtapose the actual findings against normal findings, in order to determine abnormalities or deviations from norm (if any). Optionally, and as also described above, abnormal data may be color coded or otherwise visually highlighted for display.

As another example, a clinical structured report for a blood flow examination may comprise one or more anatomical images, diagrams, line drawings, etc., of blood vessels, and may indicate blood flow, for example blood velocity and direction. For instance, for a patient suffering from stenosis of arteries (e.g. in the neck or other part of the body), a Doppler ultrasound examination as part of a carotid vascular examination may measure the flow of blood in the carotid artery, with the ultrasound measurements helping to determine a degree of narrowing of the affected blood vessel lumen. Therefore, a template for such a clinical structured report may comprise an image, diagram, line drawing, or other representation of the artery, indicating normal findings for such an examination (such as normal ranges for blood flow, normal blood flow ratios, etc.). During or after the medical examination, the system 100 would allow a user to simply confirm normal findings, or to indicate abnormal findings by drawing onto (e.g. with a computer drawing tool), or by otherwise interacting with, the diagram in order to indicate the obtained data, such as the measured blood flow through the stenosis. As with the above embodiment, this allows the user to indicate abnormal findings of the examination without having to also enter all the normal findings. Optionally, the system 100 may also be configured apply mathematical equations in order to arrive at blood flow ratios (as known in the art) in order to determine the significance of the stenosis. As with the above embodiments, template images, graphs, plots, diagrams, etc. may be used in a wide variety of structured medical report templates for a variety of medical examinations.

As another example, a clinical structured report may comprise one or more anatomical images, diagrams, line drawings, etc., of a region of anatomy, such as the brain or other organ, indicating normal ranges for the size or other characteristics of the region or organ. This allows a user of system 100 to indicate any abnormal findings of a medical examination into a clinical structured report. For example, the user may indicate an abnormal size or other characteristic of the region, or draw and indicate a size or other characteristics of an abnormal mass found in the region, for example by using a drawing tool to draw onto the provided diagram, or by choosing from one or more abnormal selections, etc.

Optionally, the present embodiments also comprise multi-language capabilities. For example, the user interface may allow the user to dynamically select among a plurality of supported languages (such as English, Spanish, German, French, etc.) and dynamically modify the user interface to present the normal findings, as well as the abnormal findings, in the user selected language. In such an embodiment, the default template would store the normal findings, as well as the collection of available abnormal findings, in the supported languages so they can be presented accordingly upon the user's language selection. Optionally, the system may be configured to receive normal and abnormal findings from the user in one language, and present and/or report them in another language. For example, the user interface may allow the findings to be entered in Spanish (or in any other supported language), and the system may then display and/or store the report in English (or in any other language). In such embodiments, the normal and abnormal findings stored in report templates may be pre-translated (i.e., "canned"), and the system may optionally provide for on-the-fly translations and/or post-process translations.

Optionally, the clinical structured report may comprise links or other resource identifiers to supplementary data. The server 101 may use such links or resource identifiers to assemble the supplementary data into the report for presentation to the user. For example, the report may contain a reproduction of one or more radiology exam images or a link to such images (not shown), audio files from the exam, video files from the exam, or other supplementary data. Such supplementary data may reside in database 104, a separate storage system, a network resource, or elsewhere.

Optionally, the server 101 distributes the clinical structured report via a public or private network such as the Internet. For example, the server may e-mail the report from one user to another, or distribute it in any other common fashion as should be obvious to one of ordinary skill in the art.

In another embodiment of the invention, the clinical structured report is electronically transmitted to a portable wireless device. For example, the report, along with any images or other data it may contain, may be transmitted to a mobile device (such as a mobile phone, laptop computer, handheld device, etc.), where it may or may not be modified by a user.

Optionally, the generation of the clinical structured report triggers generation of billing information. For example, after the generation of a report, the server may generate a bill or invoice for the examining physician's services, and send the bill or invoice to the appropriate recipient or submit it electronically according to a billing protocol.

Optionally, the clinical structured report is automatically generated by a computer-aided diagnostic tool. For example, a software program, or a combination of software and hardware elements, may study data or images obtained from clinical exams or tests residing on the database, on a network resource, or elsewhere. Once the software program identifies any medical abnormalities, or lack thereof, the reports of the present embodiments may be used to communicate any diagnoses, along with findings from such exams. A report thus created may be affirmed or disaffirmed by a reviewing physician.

While the above is a complete description of the preferred embodiments of the invention, various alternatives, modifications, and equivalents may be used. Therefore, the above description should not be taken as limiting the scope of the invention which is defined by the appended claims.

We claim:

1. A method of automatically generating clinical structured reports based on clinical structured report templates, the method implemented by one or more report management computing devices and comprising:

generating a clinical structured report template associated with medical data comprising medical examination data points and image data associated with the medical examination data points, wherein the clinical structured report template is automatically pre-populated with default normal data points corresponding to the medical examination data points and the image data associated with the medical examination data points or prior data points corresponding to prior medical examination data and prior image data associated with the medical examination points;

identifying abnormal data points in the medical data based on comparison of the default normal data points or the prior data points to the corresponding medical examination data points and the image data associated with the medical examination data points;

generating a query for data characterizing the abnormal data points;

receiving response data corresponding to the query for data characterizing the abnormal data points, wherein the received response data comprises an abnormality indicator corresponding to an association between the abnormal data points and the image data;

automatically generating a clinical structured report based on the clinical structured report template, wherein the generated clinical structured report includes modifications to the clinical structured report template based on the abnormal data points, the abnormality indicator, the response data corresponding to the abnormal data points, and the association of the abnormal data points to the image data; and generating and outputting executable instructions for graphical user interface display of the clinical structured report.

2. The method of claim 1, further comprising:

receiving supplementary data associated with the medical data comprising image data, audio data, or video data from a medical examination of a patient, or a link to medical history for the patient; and displaying the supplementary data in the clinical structured report for the patient.

3. The method of claim 1, wherein the clinical structured report template for a patient is simultaneously accessible and modifiable from a plurality of sources.

4. The method of claim 1, wherein the default normal data points and the abnormal data points are associated with anatomical data.

5. The method of claim 1, further comprising:
receiving a plurality of numerical values associated with measurements of the anatomical data over a time duration; and
displaying a graph containing a statistical based trend line based on the plurality of numerical values received.

6. The method of claim 1, further comprising:
receiving details of the patient examination over a network from a hospital network system, wherein the clinical structured report template is automatically pre-populated using the received details.

7. A clinical report data management computing device comprising:
one or more processors;
a memory coupled to the one or more processors, which are configured to execute programmed instructions stored in the memory to:
generate a clinical structured report template associated with medical data comprising medical examination data points and image data associated with the medical examination data points, wherein the clinical structured report template is automatically pre-populated with default normal data points corresponding to the medical examination data points and the image data associated with the medical examination data points or prior data points corresponding to prior medical examination data and prior image data associated with the medical examination points;
identify abnormal data points in the medical data based on comparison of the default normal data points or prior data points to the corresponding medical examination data points and the image data associated with the medical examination data points;
generate a query for data characterizing the abnormal data points;
receive response data corresponding to the query for data characterizing the abnormal data points, wherein the received response data comprises an abnormality indicator corresponding to an association between the abnormal data points and the image data;
automatically generate a clinical structured report based on the clinical structured report template, wherein the generated clinical structured report includes modifications to the clinical structured report template based on the abnormal data points, the abnormality indicator, the response data corresponding to the abnormal data points, and the association of the abnormal data points to the image data; and
generate and output executable instructions for graphical user interface display of the clinical structured report.

8. The device of claim 7, wherein the processor is further configured to be capable of executing programmed instructions comprising and stored in the memory to:
receive supplementary data associated with the medical data comprising image data, audio data, or video data from a medical examination of a patient, or a link to medical history for the patient; and
display the supplementary data in the clinical structured report for the patient.

9. The device of claim 7, wherein clinical structured report template for a patient is simultaneously accessible and modifiable from a plurality of sources.

10. The device of claim 7, wherein the default normal data points and the abnormal data points are associated with anatomical data.

11. The device of claim 7, wherein the processor is further configured to be capable of executing programmed instructions comprising and stored in the memory to:
receive a plurality of numerical values associated with measurements of the anatomical data over a time duration; and
display a graph containing a statistical based trend line based on the plurality of numerical values received.

12. The device of claim 7, wherein the processor is further configured to be capable of executing programmed instructions comprising and stored in the memory to:
receive details of a patient examination over a network from a hospital network system, wherein the clinical structured report template is automatically pre-populated using the received details.

13. A non-transitory computer readable medium having stored thereon instructions for generating clinical structured report data, comprising machine executable code which when executed by at least one processor, causes the processor to perform steps comprising:
generating a clinical structured report template associated with medical data comprising medical examination data points and image data associated with the medical examination data points, wherein the clinical structured report template is automatically pre-populated with default normal data points corresponding to the medical examination data points and the image data associated with the medical examination data points or prior data points corresponding to prior medical examination data and prior image data associated with the medical examination points;
identifying abnormal data points in the medical data based on comparison of the default normal data points or prior data points to the corresponding medical examination data points and the image data associated with the medical examination data points;
generating a query for data characterizing the abnormal data points;
receiving response data corresponding to the query for data characterizing the abnormal data points, wherein the received response data comprises an abnormality indicator corresponding to an association between the abnormal data points and the image data;
automatically generating a clinical structured report based on the clinical structured report template, wherein the generated clinical structured report includes modifications to the clinical structured report template based on the abnormal data points, the abnormality indicator, the response data corresponding to the abnormal data points, and the association of the abnormal data points to the image data;
generating and outputting executable instructions for graphical user interface display of the clinical structured report.

14. The computer readable medium of claim 13, wherein the clinical structured report template for the patient is simultaneously accessible and modifiable from a plurality of sources.

15. The computer readable medium of claim 13, wherein the default normal data points and the abnormal data points are associated with anatomical data.

16. The computer readable medium of claim 13, further having stored thereon instructions that when executed by the processor cause the processor to perform steps further comprising:
- receiving supplementary data associated with the medical data comprising image data, audio data, or video data from a medical examination of a patient, or a link to medical history for the patient; and
- displaying the supplementary data in the clinical structured report for the patient.

17. The computer readable medium of claim 13, further having stored thereon instructions that when executed by the processor cause the processor to perform steps further comprising:
- receiving a plurality of numerical values associated with measurements of the anatomical data over a time duration; and
- displaying a graph containing a statistical based trend line based on the plurality of numerical values received.

18. The computer readable medium of claim 13, further having stored thereon instructions that when executed by the processor cause the processor to perform steps further comprising:
- receiving details of the patient examination over a network from a hospital network system, wherein the clinical structured report template is automatically pre-populated using the received details.

* * * * *